(12) United States Patent
Ouyang et al.

(10) Patent No.: US 10,274,429 B2
(45) Date of Patent: Apr. 30, 2019

(54) METHOD AND SYSTEM FOR DETECTING PRECURSOR TO COATING SPALLATION

(71) Applicant: United Technologies Corporation, Farmington, CT (US)

(72) Inventors: Zhong Ouyang, Glastonbury, CT (US); Kevin D. Smith, Glastonbury, CT (US)

(73) Assignee: United Technologies Corporation, Farmington, CT (US)

( * ) Notice: Subject to any disclaimer, the term of this patent is extended or adjusted under 35 U.S.C. 154(b) by 0 days.

(21) Appl. No.: 15/706,958

(22) Filed: Sep. 18, 2017

(65) Prior Publication Data

US 2019/0086336 A1 Mar. 21, 2019

(51) Int. Cl.
*G01N 21/71* (2006.01)
*G01N 21/84* (2006.01)
*G01N 21/17* (2006.01)

(52) U.S. Cl.
CPC ......... *G01N 21/71* (2013.01); *G01N 21/8422* (2013.01); *G01N 2021/1765* (2013.01); *G01N 2021/8427* (2013.01)

(58) Field of Classification Search
CPC ............... G01N 21/71; G01N 21/8422; G01N 2021/8427; G01N 2021/1765
USPC ........................................................ 250/349
See application file for complete search history.

(56) References Cited

U.S. PATENT DOCUMENTS

| 4,647,220 | A | 3/1987 | Adams et al. |
| 6,184,528 | B1 | 2/2001 | DiMarzio et al. |
| H2127 | H | 10/2005 | Byrd |
| 7,044,636 | B2 * | 5/2006 | Taketoshi ........... G01N 21/1717 356/432 |
| 7,425,093 | B2 | 9/2008 | Wickersham, Jr. et al. |
| 7,690,840 | B2 | 4/2010 | Zombo et al. |
| 7,769,201 | B2 | 8/2010 | Sun |
| 9,518,918 | B2 | 12/2016 | Mann et al. |
| 9,519,844 | B1 | 12/2016 | Thompson et al. |
| 2008/0317090 | A1 | 12/2008 | Tralshawala et al. |
| 2012/0050537 | A1 * | 3/2012 | Ringermacher ... G01B 11/0658 348/164 |

(Continued)

FOREIGN PATENT DOCUMENTS

EP 1726943 A1 12/2006

*Primary Examiner* — David P Porta
*Assistant Examiner* — Gisselle M Gutierrez
(74) *Attorney, Agent, or Firm* — Kinney & Lange, P.A.

(57) ABSTRACT

Apparatus and associated methods relate to predicting precursor to coating spallation. Heat is provided to a first surface of a member. A time sequence of thermal images is captured of the first surface and/or a second surface of the member. Each of the images includes a two-dimensional array of image data. Each of the image data of the two-dimensional array of image data corresponds to an xy-coordinate pair. A two-dimensional array of thermal diffusivities is calculated based on the captured time sequence of thermal images. Each of the thermal diffusivities of the two-dimensional array of thermal diffusivities corresponds to the xy-coordinate pair. Each of the calculated thermal diffusivities of the two dimensional array of thermal diffusivities are compared with a predetermined threshold. If the calculated thermal diffusivity is greater than the predetermined threshold, then precursor to coating spallation of the thermal barrier coating at the corresponding xy-coordinate pair is predicted.

16 Claims, 7 Drawing Sheets

(56) References Cited

U.S. PATENT DOCUMENTS

| | | | |
|---|---|---|---|
| 2014/0067185 A1* | 3/2014 | Tralshawala | G01R 33/12 701/24 |
| 2016/0003734 A1* | 1/2016 | Mann | G01N 17/006 250/339.05 |
| 2016/0301880 A1 | 10/2016 | Iyer et al. | |

* cited by examiner

METHOD AND SYSTEM FOR DETECTING PRECURSOR TO COATING SPALLATION

BACKGROUND

Thermal barrier coatings (TBCs) are applied to metallic components and are used to protect such metallic components from large and/or prolonged heat exposure. Various such coated metallic components can be used in aircraft engines, such as gas turbine engines. These thermal barrier coatings can promote heat protection by utilizing materials that can sustain an appreciable temperature difference between the coating surface and the underlying metallic component. Thermal barrier coatings can permit the coated metallic components to operate at higher temperatures than uncoated equivalent metallic component can be operated.

Use of these thermal barrier coatings can change the thermal diffusivity of the metallic component. The thermal diffusivity is defined as the thermal conductivity divided by density and specific heat capacity at constant pressure. Thermal diffusivity is a metric indicative of rate of heat transfer through a component from a hot surface to a cold surface. A high value of thermal diffusivity indicates that heat is transferred more readily through the component, whereas a low value of thermal diffusivity indicates that heat is transferred less readily through the component.

Low values of thermal diffusivity permit a higher thermal gradient to be maintained across the metallic component. Such high thermal gradients thereby permit a low-temperature surface of the metallic component to operate at a relatively low-temperature, even while the high-temperature surface of the metallic component is being exposed to very-high temperatures. Such control of component temperature profile can result in extended part life by reducing oxidation and thermal fatigue, for example.

Thermal barrier coatings can separate from a bond coating and/or from the underlying metallic component upon which it has been formed. Various mechanisms can cause such separation of the coating from its component. For example, compression waves can cause the coating to separate from the component via spallation. When the coating separates from the underlying component, control of the temperature profile across the metallic component is reduced. Furthermore, the coating can be entirely separated from the component, break off, and be ingested by an aircraft engine, for example. Such ingestion of spalled coating materials can cause damage to the equipment ingesting such materials. There is a need to better predict when coating spallation is imminent.

SUMMARY

Apparatus and associated methods relate to a system for predicting precursor to coating spallation. The system includes a heat source configured to provide heat to a first surface of a member having a coating on the first surface and/or a second surface. The system includes a thermographic camera configured to capture a time sequence of thermal images of the first surface or of the second surface of the member. Each of the time sequence of thermal images includes a two-dimensional array of image data. Each of the image data of the two-dimensional array of image data corresponds to an xy-coordinate pair. The time sequence of thermal images is indicative of thermal diffusivities of respective xy-locations of the member. The system also includes a spallation predictor configured to compare each of the thermal diffusivities of the member at the xy-locations and a predetermined threshold. If the calculated thermal diffusivity is greater than the predetermined threshold, then the spallation predictor is configured to predict precursor to coating spallation of the coating at the respective xy-location.

Some embodiments relate to a method for predicting precursor to coating spallation. In the method heat is provided to a first surface of a member having a coating on the first surface and/or a second surface. Then a time sequence of thermal images of the first surface or of the second surface of the member is captured. Each of the time sequence of thermal images includes a two-dimensional array of image data. Each of the two-dimensional array of image data corresponds to an xy-coordinate pair. Then, a two-dimensional array of thermal diffusivities is calculated based on the captured time sequence of thermal images. Each of the two-dimensional array of thermal diffusivities corresponds to an xy-coordinate pair. Then, each of the calculated thermal diffusivities of the two dimensional array of thermal diffusivities is compared with a predetermined threshold. Then, if the calculated thermal diffusivity is greater than the predetermined threshold, precursor to coating spallation at the corresponding xy-coordinate pair is predicted.

Some embodiments relate to a system for predicting precursor to coating spallation. The system includes a heat source, a thermographic camera, one or more processors, and one or more storage devices. The one or more storage devices are encoded with instructions that, when executed by the one or more processors, cause the system to provide, via the heat source, heat to a first surface of a member having a coating on the first surface and/or a second surface. The one or more storage devices are further encoded with instructions that, when executed by the one or more processors, cause the system to capture, via the thermographic camera, a time sequence of thermal images of the first surface or of the second surface of the member. Each of the time sequence of thermal images includes a two-dimensional array of image data. Each of the two-dimensional array of image data corresponds to an xy-coordinate pair. The one or more storage devices are further encoded with instructions that, when executed by the one or more processors, cause the system to calculate, based on the captured time sequence of thermal images, a two-dimensional array of thermal diffusivities. Each of the two-dimensional array of thermal diffusivities corresponds to an xy-coordinate pair. The one or more storage devices are further encoded with instructions that, when executed by the one or more processors, cause the system to compare each of the calculated thermal diffusivities of the two dimensional array of thermal diffusivities with a predetermined threshold. If the calculated thermal diffusivity is greater than the predetermined threshold, then the system is configured to predict precursor to coating spallation of the thermal barrier coating at the corresponding xy-coordinate pair.

DETAILED DESCRIPTION

Apparatus and associated methods relate to predicting precursor to coating spallation. Heat is provided to a first surface of a member. A time sequence of thermal images is captured of the first surface and/or a second surface of the member. Each of the images includes a two-dimensional array of image data. Each of the image data of the two-dimensional array of image data corresponds to an xy-coordinate pair. A two-dimensional array of thermal diffusivities is calculated based on the captured time sequence of thermal images. Each of the thermal diffusivities of the two-dimensional array of thermal diffusivities corresponds to the xy-coordinate pair. Each of the calculated thermal diffusivities of the two dimensional array of thermal diffusivities are compared with a predetermined threshold. If the calculated thermal diffusivity is greater than the predetermined threshold, then precursor to coating spallation of the thermal barrier coating at the corresponding xy-coordinate pair is predicted.

Figure 1:
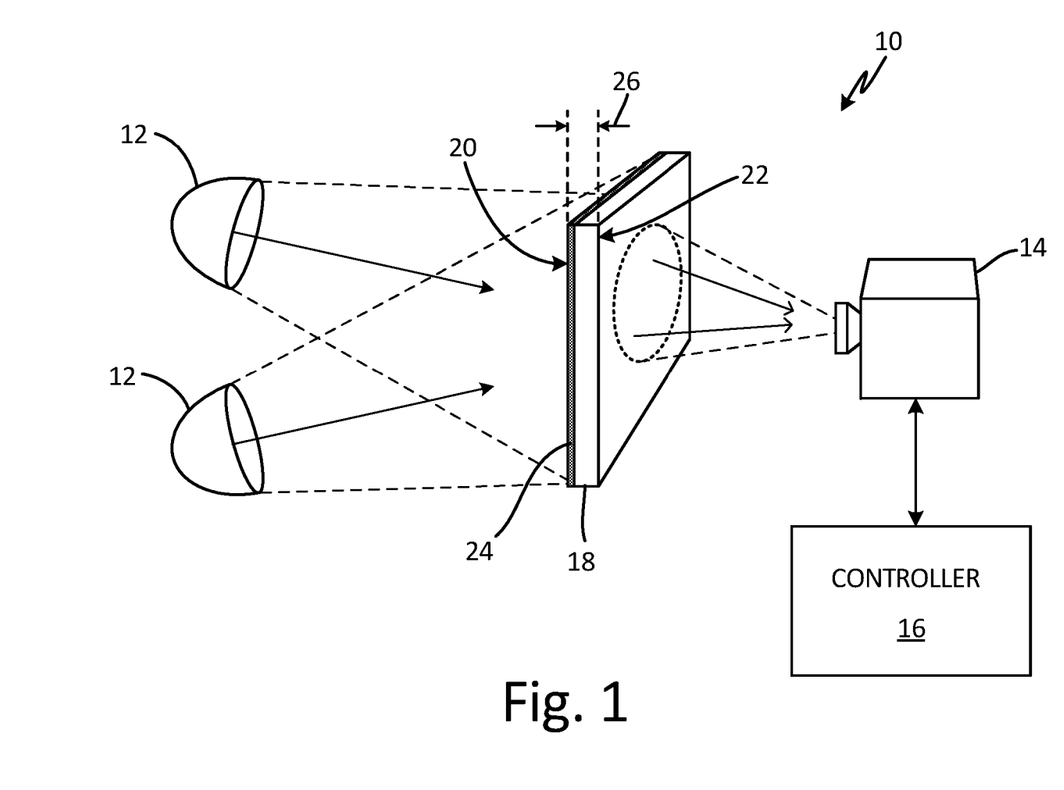
FIG. 1 is a schematic diagram of a member being tested by an embodiment of a spallation prediction system using through-transmission thermography.

FIG. 1 is a schematic diagram of a member being tested by an embodiment of a spallation prediction system using through-transmission thermography. In FIG. 1, spallation prediction system 10 includes heat source(s) 12, thermographic camera 14, and controller 16. Member 18 is configured to be tested by spallation prediction system 10. Member 18 has first surface 20 exposed to heat source(s) 12 and second surface 22 exposed to thermographic camera 14. First surface 20 has thermal barrier coating 24 formed thereon. Member 18 is positioned between heat source(s) 12 and thermographic camera 14, which is the testing configuration used for through-transmission thermography. Heat source(s) 12 project a temporally changing amount of heat onto first surface 20 of member 18. A portion of the projected heat is absorbed by member 18 and then is conducted through thickness 26 of member 18. A temperature of second surface 22 of member 18 then changes in response to the transmitted heat thereto. Thermographic camera 14 captures a time sequence of images of second surface 22. A model of heat conduction through member 18 can be fit to the captured sequence of images, and a thermal diffusivity of member 18 can be calculated.

Figure 2:
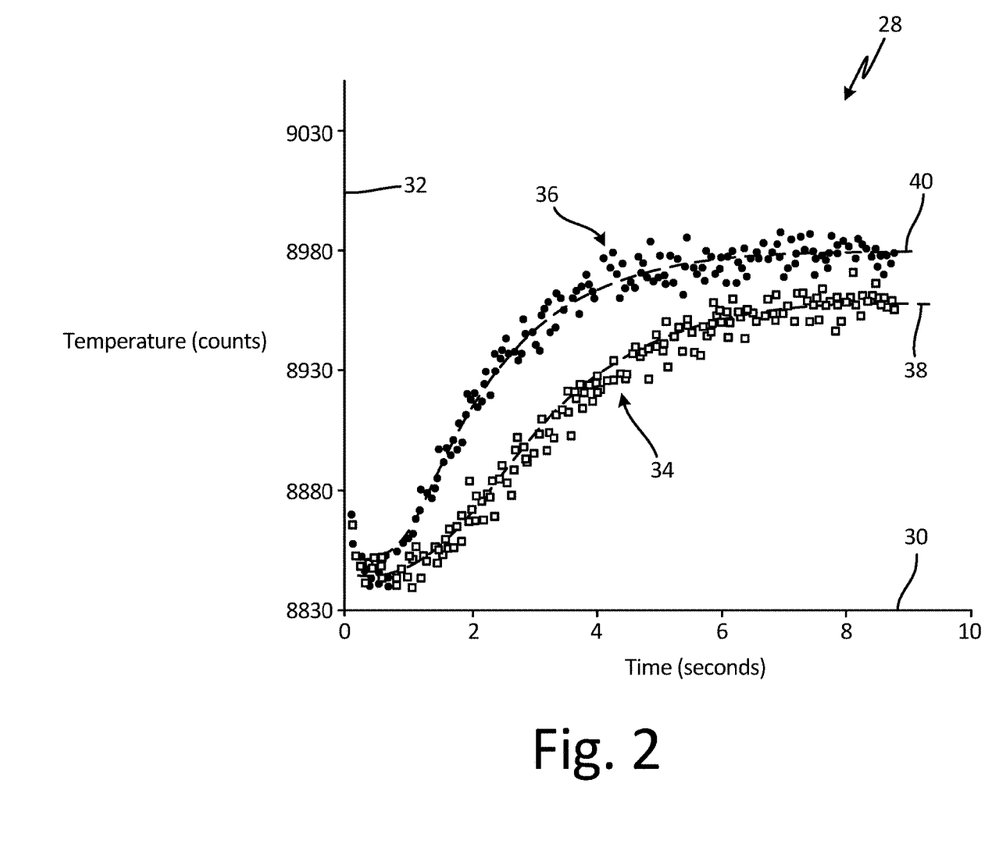
FIG. 2 is a graph of a time sequence of image data generated by a pixel imaging a location of a member under test by the through-transmission thermography setup of FIG. 1.

FIG. 2 is a graph of a time sequence of image data generated by a pixel imaging a location of a member under test by the through-transmission thermography setup of FIG. 1. In FIG. 2, graph 28 includes horizontal axis 30, vertical axis 32, data sets 34 and 36, and respective fitted curves 38 and 40. Horizontal axis 30 is indicative of a time at which an image is captured by thermographic camera 14 (shown in FIG. 1). Vertical axis 32 is indicative of temperature of second surface 22 as measured by thermographic camera 14. Data set 34 corresponds to a temperature of second surface 22 at a location that is imaged onto a single pixel of thermographic camera 14. Data set 34 is a response to a time-varying function of heat (e.g., a step or delta function) projected by heat source(s) 12 onto first surface 20 of member 18. Data set 34 was taken of a newly manufactured member, such as, for example, a combustor panel of an aircraft engine. Fitted curve 38 corresponds to a thermodynamic model of a temperature response of second surface 22 to the time-varying function of heat projected onto first surface 20. The parameters of fitted curve 38 have been selected to best fit data set 34. In one example, the thermal diffusivity of member 18 has a thermal diffusivity of 0.0055 $cm^2$/sec as determined in this way.

Member 18 was then subjected to an aging process, in which member 18 is heated to an elevated temperature of approximately 1400° F. for a duration of 100 hours. Then, data set 36 was obtained after the aging process was completed. Data set 36 is again a response to a delta function (i.e., a 3 msec pulse) of heat projected by heat source(s) 12 onto first surface 20 of member 18. Data set 36 corresponds to a temperature of second surface 22 at the location that is imaged onto the same single pixel of thermographic camera 14 that was used to generate data set 34. Fitted curve 40 corresponds to a thermodynamic model of a temperature response of second surface 22 to the delta function of heat projected onto first surface 20. The parameters of fitted curve 40 have been selected to best fit data set 36. In one example, the thermal diffusivity of member 18 has a thermal diffusivity of 0.0087 $cm^2$/sec as determined in this way. Thus, the aging process has caused the thermal diffusivity of member 18 to increase (e.g., from 0.0055 $cm^2$/sec to 0.0087 $cm^2$/sec). Such an increase in the thermal diffusivity of member 18 can be indicative of deterioration in thermal barrier coating 24 (shown in FIG. 1) of member 18.

Figure 3:
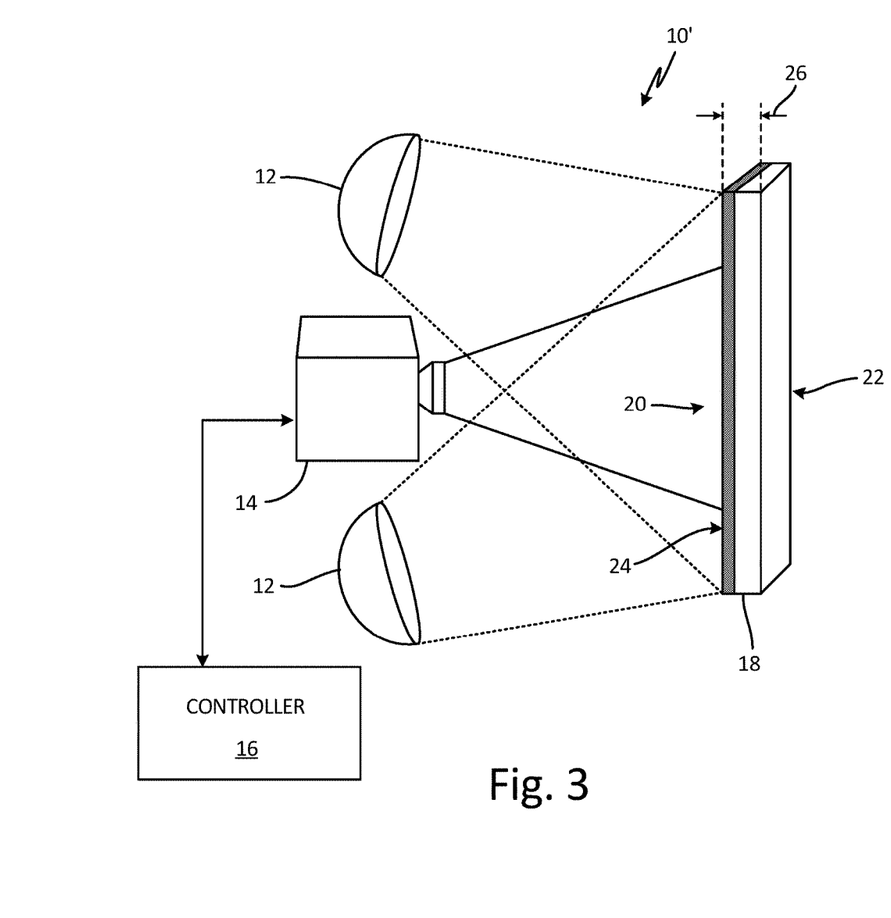
FIG. 3 is a schematic diagram of a member being tested by an embodiment of a spallation prediction system using pulse echo thermography.

Other methods of measuring the thermal diffusivity of member 18 can be performed. For example, FIG. 3 is a schematic diagram of a member being tested by an embodiment of a spallation prediction system using pulse echo thermography. In FIG. 3, spallation prediction system 10' includes heat source(s) 12, thermographic camera 14, and controller 16. Member 18 is configured to be tested by spallation prediction system 10'. Member 18 has first surface 20 exposed to heat source(s) 12 and also exposed to thermographic camera 14. First surface 20 has thermal barrier coating 24 formed thereon. Member 18 is positioned such that both heat source(s) 12 and thermographic camera 14 are on the same side of member 18, which is the testing configuration used for pulse echo thermography using plane heating of member 18.

Heat source(s) 12 project a temporally changing amount of heat onto first surface 20 of member 18. A portion of the projected heat is absorbed by member 18 and then is conducted through thickness 26 of member 18. As heat is conducted away from first surface 20, the temperature of first surface 20 changes. For example, if a pulse of heat is projected onto first surface 20, first surface 20 will experience a temperature increase in response to the projected pulse of heat. After the pulse of heat is no longer being transmitted, first surface 20 will then have a decreasing temperature as the heat is conducted through thickness 26 to second surface 22 of member 18. Thermographic camera 14 captures a time sequence of images of first surface 20. A thermodynamic model of the system can be made and fit to the temperature data of first surface 20 as measured by thermographic camera 14. The thermal diffusivity of member 18 can then be calculated based upon the fitted curve parameters.

In this way, each of the time sequence of images captured by thermographic camera 14 can be indicative of a thermal diffusivity of member 18. The thermal diffusivity of member 18 spatially can vary over the dimensions of member 18 due to local variation of barrier coating 24, for example. Using a thermodynamic model, a modeled temperature of member 18 can be calculated for various heating and barrier coating conditions. A time sequence of the modeled temperature of member 18 can then be compared to the time sequence of images captured by thermographic camera 14. The comparison of the time sequence of images to the time sequence of modeled temperature of member 18 can be used to determine the thermal diffusivity of member 18. If the comparison reveals regions of member 18 have a thermal diffusivity that are greater than a predetermined threshold, precursor to coating spallation can be predicted for such regions.

Figure 4:
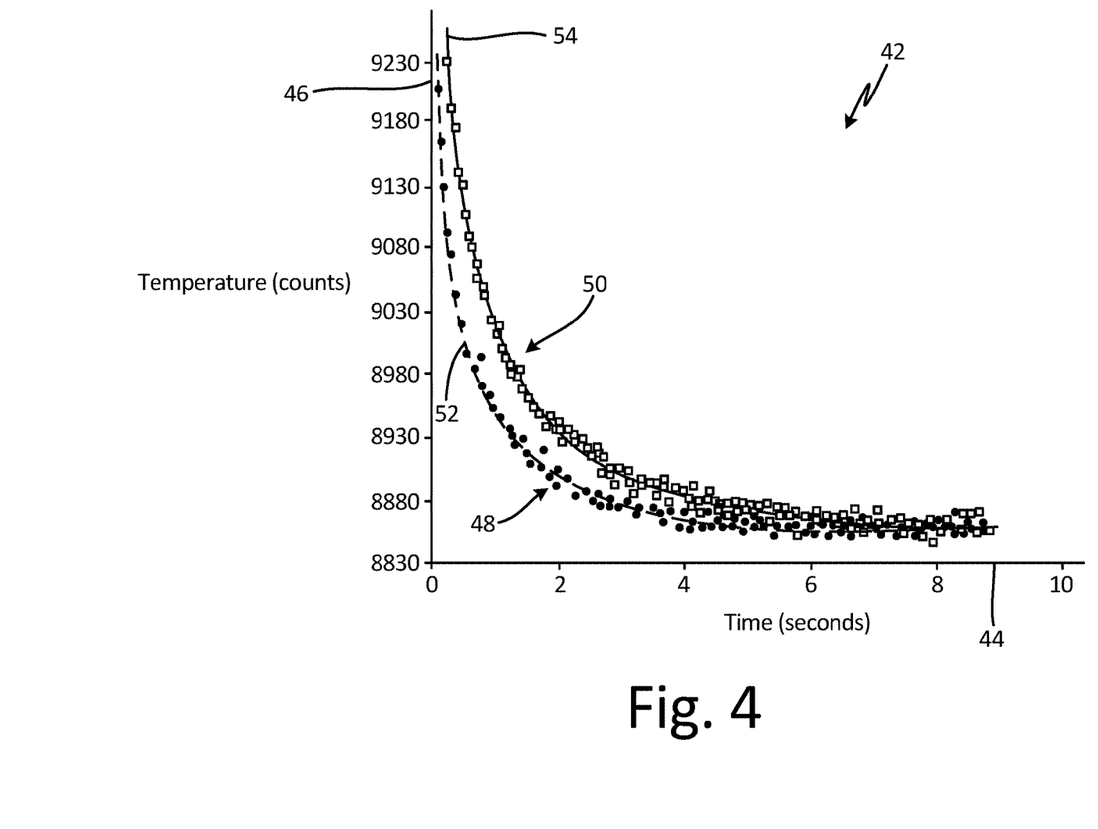
FIG. 4 is a graph of a time sequence of image data generated by a pixel imaging a different location or member under test by the pulse echo thermography setup of FIG. 3.

FIG. 4 is a graph of a time sequence of image data generated by a pixel imaging a location or member under test by the pulse echo thermography setup of FIG. 3. In FIG. 4, graph 42 includes horizontal axis 44, vertical axis 46, data sets 48 and 50, and respective fitted curves 52 and 54. Horizontal axis 44 is indicative of a time at which an image is captured by thermographic camera 14 (shown in FIG. 3). Vertical axis 46 is indicative of temperature of second surface 22 as measured by thermographic camera 14. Data set 48 corresponds to a temperature of first surface 20 at a location that is imaged onto a single pixel of thermographic camera 14. Data set 48 is a response to a pulse of heat projected by heat source(s) 12 onto first surface 20 of member 18. Data set 48 was taken of a newly manufactured member, such as, for example, a turbine or compressor blade of an aircraft engine. Fitted curve 52 corresponds to a thermodynamic model of a temperature response of first surface 20 to the pulse of heat projected thereon. The parameters of fitted curve 52 have been selected to best fit data set 48. In one example, the thermal diffusivity of member 18 has a thermal diffusivity of 0.0060 $cm^2$/sec as determined in this way.

Member 18 was then subjected to an aging process, in which member 18 is heated to an elevated temperature of approximately 1400° F. for a duration of 100 hours. Then, data set 50 was obtained after the aging process was completed. Data set 50 is again a response to a pulse of heat projected by heat source(s) 12 onto first surface 20 of member 18. Data set 50 corresponds to a temperature of first surface 20 at the location that is imaged onto the same single pixel of thermographic camera 14 that was used to generate data set 48. Fitted curve 40 corresponds to a thermodynamic model of a temperature response of first surface 20 to the pulse of heat projected thereon. In one example, the parameters of fitted curve 54 have been selected to best fit data set 50. The thermal diffusivity of member 18 has a thermal diffusivity of 0.0094 $cm^2$/sec as determined in this way. Thus, the aging process has caused the thermal diffusivity of member 18 to increase (e.g., from 0.0060 $cm^2$/sec to 0.0094 $cm^2$/sec). Such an increase in the thermal diffusivity of member 18 can be indicative of deterioration in thermal barrier coating 24 (shown in FIG. 3) of member 18.

Figure 5:
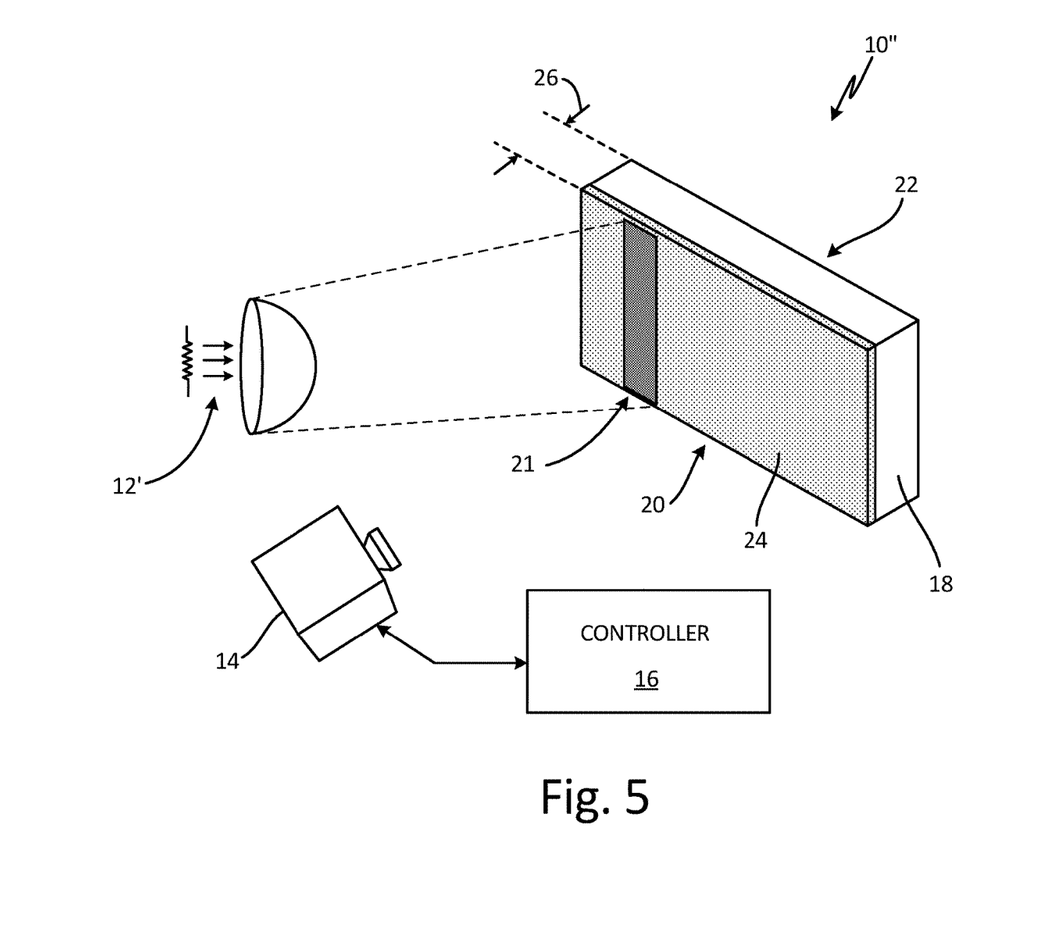
FIG. 5 is a schematic diagram of an embodiment of a thermography setup configured to generate heating of only a local portion of a member.

FIG. 5 is a schematic diagram of an embodiment of a thermography setup configured to generate heating of only a local portion of a member. In FIG. 5, still another method of determining the thermal diffusivity of member 18 is depicted. In. FIG. 5, spallation prediction system 10" includes heat source(s) 12', thermographic camera 14, and controller 16. Member 18 is configured to be tested by spallation prediction system 10". In the FIG. 5 embodiment, heat source(s) 12' is configured so as to provide heat to controlled portion 21 of first surface 20 of member 18. Heat source(s) 12' can have a focusing mechanism, for example, and/or capability of directing a beam of energy so as to heat only controlled portion 21.

Member 18 has first surface 20 exposed to both heat source(s) 12' and thermographic camera 14. Heat source(s) 12' and thermographic camera 14 are positioned on the same side of member 18, which is the testing configuration used for pulse echo thermography using line heating (e.g. heating only controlled portion 21 of first surface 20) of member 18. Heat source(s) 12' project a temporally changing amount of heat onto first surface 20 of member 18. A portion of the projected heat is absorbed at controlled portion 21 of first surface 20 and then is conducted through thickness 26 of member 18. The absorbed heat is then conducted both through thickness 26 of member 18 and laterally along surface 20. The temperature of first surface 20 of member 18 then changes in response to the transmitted heat. Thermographic camera 14 captures a time sequence of images of first surface 20. A thermodynamic model of the system can be made and fit to the temperature data of first surface 20 as measured by thermodynamic camera 14. Thermal diffusivities of various locations of member 18 can then be calculated based upon the fitted curve parameters. The calculated thermal diffusivities of the various locations of member 18 can be compared with a predetermined threshold. If the comparison reveals that a region(s) of member 18 has a thermal diffusivity that is greater than the predetermined threshold, precursor to coating spallation can be predicted at such region(s).

Figure 6:
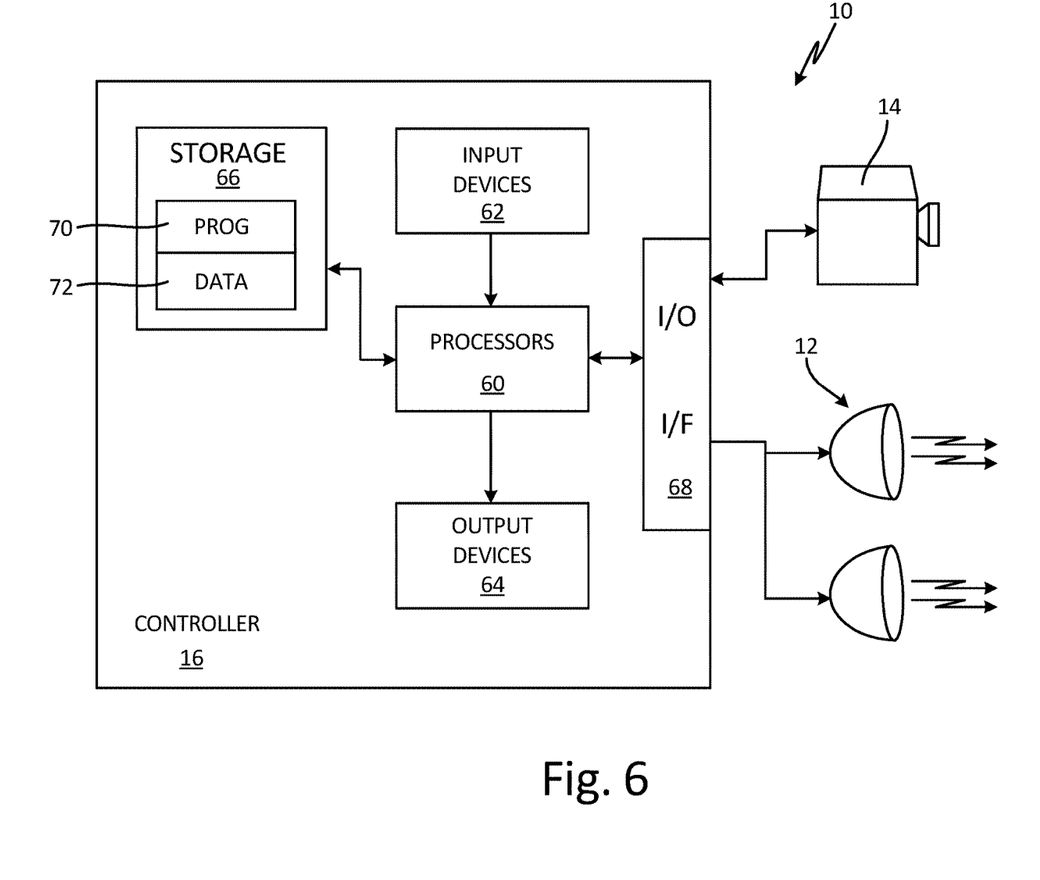
FIG. 6 is a block diagram of an exemplary system for predicting precursor to coating spallation.

FIG. 6 is a block diagram of an exemplary system for predicting precursor to coating spallation. In FIG. 6, spallation prediction system 10 includes heat source(s) 12, thermographic camera 14, and controller 16. Controller 16 includes processor(s) 60, input devices 62, output devices 64, storage device(s) 66, and input/output interface 68. Storage device(s) 66 has various storage or memory locations. Storage device(s) 66 includes program memory 70, and data memory 72. However, in certain examples, controller 16 can include more or fewer components. For instance, in examples where controller 16 is an avionics system, controller 16 may not include input devices 62 and/or output devices 64. Controller 16 may include additional components such as a battery that provides power to components of controller 16 during operation.

Processor(s) 60, in one example, is configured to implement functionality and/or process instructions for execution within controller 16. For instance, processor(s) 60 can be capable of processing instructions stored in storage device(s) 66. Examples of processor(s) 60 can include any one or more of a microprocessor, a controller, a digital signal processor (DSP), an application specific integrated circuit (ASIC), a field-programmable gate array (FPGA), or other equivalent discrete or integrated logic circuitry.

Input/output interface 68, in some examples, includes a communications module. Input/output interface 68, in one example, utilizes the communications module to communicate with external devices via one or more networks, such as one or more wireless or wired networks or both. The communications module can be a network interface card, such as an Ethernet card, an optical transceiver, a radio frequency transceiver, or any other type of device that can send and receive information. The communications module can be a network interface card, such as an Ethernet card, an optical transceiver, a radio frequency transceiver, or any other type of device that can send and receive information. Other examples of such network interfaces can include Bluetooth, 3G, 4G, and Wi-Fi radio computing devices as well as Universal Serial Bus (USB). In some embodiments, communication with the aircraft can be performed via a communications protocol, such as, for example, an Aeronautical Radio, Incorporated (ARINC) standard communications protocol. In an exemplary embodiment, aircraft communication with the aircraft can be performed via a communications bus, such as, for example, a Controller Area Network (CAN) bus.

Storage device(s) 66 can be configured to store information within controller 16 during operation. Storage device(s) 66, in some examples, is a computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, storage device(s) 66 is a temporary memory, meaning that a primary purpose of storage device(s) 66 is not long-term storage. Storage device(s) 66, in some examples, is described as volatile memory, meaning that storage device(s) 66 do not maintain stored contents when power to controller 16 is turned off. Examples of volatile memories can include random access memories (RAM), dynamic random access memories (DRAM), static random access memories (SRAM), and other forms of volatile memories. In some examples, storage device(s) 66 is used to store program instructions for execution by processor(s) 60. Storage device(s) 66, in one example, is used by software or applications running on controller 16 (e.g., a software program implementing long-range cloud conditions detection) to temporarily store information during program execution.

Storage device(s) 66, in some examples, also include one or more computer-readable storage media. Storage device(s) 66 can be configured to store larger amounts of information than volatile memory. Storage device(s) 66 can further be configured for long-term storage of information. In some examples, Storage device(s) 66 include non-volatile storage elements. Examples of such non-volatile storage elements can include magnetic hard discs, optical discs, flash memories, or forms of electrically programmable memories (EPROM) or electrically erasable and programmable (EEPROM) memories.

Input devices 62, in some examples, are configured to receive input from a user. Examples of input devices 62 can include a mouse, a keyboard, a microphone, a camera device, a presence-sensitive and/or touch-sensitive display, push buttons, arrow keys, or other type of device configured to receive input from a user. In some embodiments, input communication from the user can be performed via a communications protocol, such as, for example, an Aeronautical Radio, Incorporated (ARINC) standard communications protocol. In an exemplary embodiment, user input communication from the user can be performed via a communications bus, such as, for example, a Controller Area Network (CAN) bus.

Output devices 64 can be configured to provide output to a user. Examples of output devices 64 can include a display device, a sound card, a video graphics card, a speaker, a cathode ray tube (CRT) monitor, a liquid crystal display (LCD), a light emitting diode (LED) display, an organic light emitting diode (OLED) display, or other type of device for outputting information in a form understandable to users or machines. In some embodiments, output communication to the user can be performed via a communications bus, such as, for example, an Aeronautical Radio, Incorporated (ARINC) standard communications protocol. In an exemplary embodiment, output communication to the user can be performed via a communications bus, such as, for example, a Controller Area Network (CAN) bus.

In some embodiments, spallation prediction system 10 can be configured to be permanently mounted to an aircraft engine. In other embodiments, spallation prediction system 10 can be configured as a mobile test unit that interfaces with an aircraft engine at times determined by a maintenance schedule. In some embodiments, spallation prediction system 10 can be configured to test turbine blades and/or compressor blades, which have a thermal barrier coating. Other thermal barrier coated members can be tested as well, using spallation prediction system 10.

Figure 7:
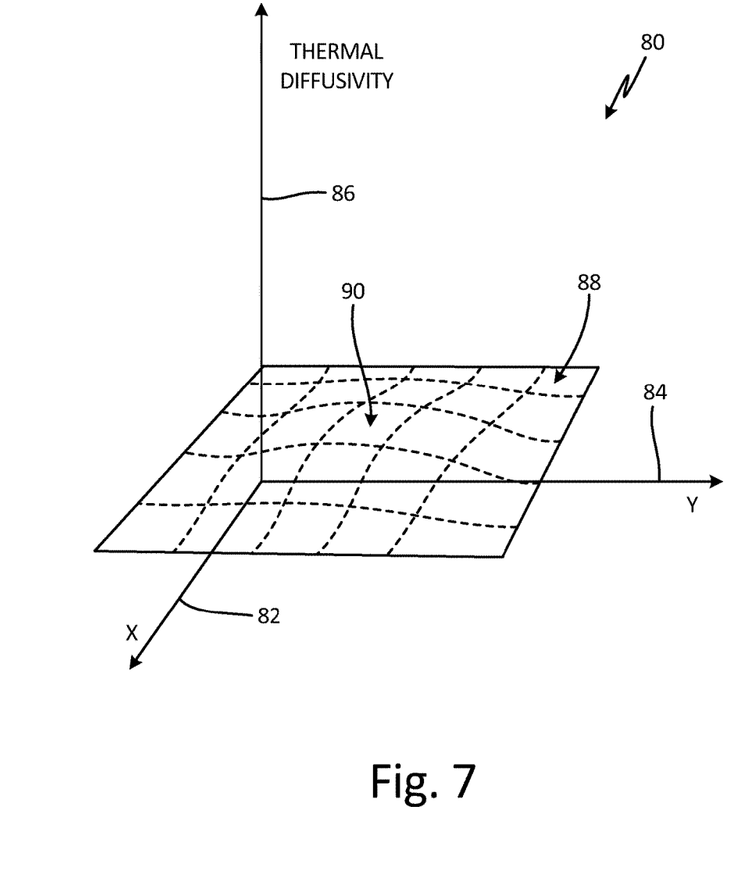
FIG. 7 is a graph of a thermal diffusivity of a member as a function of a surface location of the member.

FIG. 7 is a graph of a thermal diffusivity of a member as a function of a surface location of the member. In FIG. 7, graph 80 includes x-axis 82, y-axis 84, z-axis 86, and thermal diffusivity data set 88. FIG. 7 depicts the thermal diffusivities corresponding to a two-dimensional array of locations corresponding to a two-dimensional array of pixels of thermographic camera 14 (shown in FIG. 6). X-axis 82 is indicative of an x-coordinate of a surface of a tested member. The x-coordinate is associated with locations along a surface of member 18, from which heat is radiated and then imaged upon a corresponding row of pixels of thermographic camera 14. Y-axis 84 is indicative of a y-coordinate of a surface of the tested member. The y-coordinate is associated with locations along the surface of member 18, from which heat is radiated and then imaged upon a corresponding column of pixels of thermographic camera 14. Z-axis 86 is indicative of a thermal diffusivity of member 18 as calculated for each of the surface locations indicated by the x-coordinates and y-coordinates.

Thermal diffusivity data set 88 depicts the relation between the calculated thermal diffusivity of the tested member and the surface location of the tested member. As depicted in graph 80, thermal diffusivity data set 88 shows local peak 90 of thermal diffusivity. Local peak 90 may be indicative of a degradation of a thermal barrier coating. If, for example, one or more calculations of thermal diffusivity corresponding to one or more pixels, respectively, have a value that is greater than a predetermined threshold, then processor(s) 60 (shown in FIG. 6) will determine that degradation of the thermal barrier coating has occurred.

In some embodiments, the predetermined threshold can be geometrically related to an initial thermal diffusivity of the member as measured during manufacture of the member. For example, in some embodiments, the predetermined threshold can be 120%, 125%, 133%, 150%, or 200% of the initial thermal diffusivity of the member. In some embodiments, precursor to coating spallation is predicted if data from a single pixel results in the thermal diffusivity calculated for the corresponding location on the member to exceed the predetermined threshold. In some embodiments, the number of pixels, which correspond to calculated thermal diffusivities exceeding the predetermined threshold must exceed a predetermined count for precursor to coating spallation to be predicted. In some embodiments, the number of contiguous pixels, which correspond to calculated thermal diffusivities exceeding the predetermined threshold must exceed a predetermined count for precursor to coating spallation to be predicted.

Processor(s) 60 can then predict a precursor to coating spallation, based on the pixel data of the two-dimensional array of pixels of thermographic camera 14. In some embodiments, processor(s) 60 can generate a signal indicative of precursor to coating spallation. In some embodiments, processor(s) 60 can output an alarm signal if precursor to coating spallation is predicted.

Discussion of Possible Embodiments

The following are non-exclusive descriptions of possible embodiments of the present invention.

Apparatus and associated methods relate to a system for predicting precursor to coating spallation. The system includes a heat source configured to provide heat to a first surface of a member having a coating formed on the first surface and/or a second surface. The system includes a thermographic camera having a focal plane array comprising a two-dimensional array of pixels, each at a location associated with an xy-coordinate pair. The thermographic camera is configured to receive heat radiated from the first surface or from the second surface of the member and to focus the received heat onto the focal plane array, thereby forming an image of the first surface or of the second surface of the member. The thermographic camera is further configured to capture a time sequence of thermal images of the first surface or of the second surface of the member. The time sequence of thermal images is indicative of thermal diffusivities of the member at respective xy-locations. The system also includes a spallation predictor configured to predict, based on a comparison of the thermal diffusivities of the member at the respective xy-locations and a predetermined threshold, precursor to coating spallation.

A heat source configured to provide heat to a first surface of a member can be, for example, a heat source that, during operation, is located proximate the surface of the member and radiates thermal energy onto the first surface of the member.

A thermographic camera configured to receive heat radiated from the first surface or from the second surface of the member and to focus the received heat onto the focal plane array can be, for example, a thermographic camera that, during operation, is has an optical axis aligned with the member such that the first or second surface of the member is imaged onto a focal plane array of the camera.

A thermal diffusivity calculator configured to calculate, based on the captured time sequence of thermal images, a two-dimensional array of thermal diffusivities can be, for example, a processor that, during operation, calculates, based on the captured time sequence of thermal images, a two-dimensional array of thermal diffusivities, each of which corresponds to one of a two-dimensional array of pixels.

A spallation predictor configured to predict, based on the calculated thermal diffusivities, precursor to coating spallation of the coating at the corresponding xy-coordinate pair can be, for example, a spallation predictor that, during operation, predicts, based on the calculated thermal diffusivities, precursor to coating spallation of the coating at the corresponding xy-coordinate pair.

The system of the preceding paragraph can optionally include, additionally and/or alternatively, any one or more of the following features, configurations and/or additional components:

A further embodiment of the foregoing system can further include a thermal diffusivity calculator configured to calculate, based on the captured time sequence of thermal images, a two-dimensional array of thermal diffusivities, each of the two-dimensional array of thermal diffusivities corresponding to the xy-coordinate pair of one of the pixels of the two-dimensional array of pixels.

A further embodiment of any of the foregoing systems, wherein the coating can be a thermal barrier coating.

A further embodiment of any of the foregoing systems, wherein the thermographic camera can be configured to capture the time sequence of thermal images of the first surface of the member, thereby acting as a pulse-echo thermal-imager, and heat being generated as a temporal pulse of heat.

A thermographic camera configured to capture the time sequence of thermal images can be, for example, a thermographic camera that, during operation, captures the time sequence of thermal images.

A further embodiment of any of the foregoing systems, wherein the heat thermographic camera can be configured to capture the time sequence of thermal images of the second surface of the member, thereby acting as a through-transmission thermal-imager. The provided heat can be generated as a temporal step of heat.

A further embodiment of any of the foregoing systems, wherein the spallation predictor can be further configured to output an alarm signal, if precursor to coating spallation is predicted.

A spallation predictor configured to output an alarm can be, for example, a spallation predictor that, during operation, outputs an alarm, such as, for example, a signal indicative of an alarm condition.

A further embodiment of any of the foregoing systems, wherein the spallation predictor can predict precursor to coating spallation in response to one of the calculated thermal diffusivities exceeding a predetermined value.

A further embodiment of any of the foregoing systems, wherein the spallation predictor can predict precursor to coating spallation is predicted in response to a number of pixels, which correspond to calculated thermal diffusivities exceeding a predetermined threshold, exceeding a predetermined count.

A further embodiment of any of the foregoing systems, wherein the heat source and the thermographic camera can be configured to mount to an aircraft proximate the member having the coating.

A thermographic camera configured to mount to an aircraft proximate the member having the coating can be, for example, a camera having a mounting system that can couple to a complementary mounting fixture proximate the member having a coating.

A further embodiment of any of the foregoing systems, wherein the coating can be on the first surface of the member.

A further embodiment of any of the foregoing systems, wherein the heat can be provided in a substantially spatially uniform manner to the first surface of the member.

A further embodiment of any of the foregoing systems, wherein the member can be a plate member and the first and second surfaces are opposite to one another and separated from one another by a thickness of the plate member.

Some embodiments relate to a method for predicting precursor to coating spallation. The method includes providing heat to a first surface of a member having a coating on the first surface and/or a second surface. The method includes capturing a time sequence of thermal images of the first surface or of the second surface of the member. Each of the time sequence of thermal images includes a two-dimensional array of pixel data. Each of the two-dimensional array of pixel data corresponds to an xy-coordinate pair. The method includes calculating, based on the captured time sequence of thermal images, a two-dimensional array of thermal diffusivities. Each of the two-dimensional array of thermal diffusivities corresponds to the xy-coordinate pair. The method includes comparing each of the calculated thermal diffusivities of the two dimensional array of thermal diffusivities with a predetermined threshold. The method also includes predicting, based on the calculated thermal diffusivities, precursor to coating spallation at the corresponding xy-coordinate pair.

The method of the preceding paragraph can optionally include, additionally and/or alternatively, any one or more of the following features, configurations and/or additional components:

A further embodiment of the foregoing method can further include outputting an alarm signal if precursor to coating spallation is predicted.

A further embodiment of any of the foregoing methods, wherein predicting precursor to coating spallation can further include comparing the calculated thermal diffusivities with a predetermined value.

A further embodiment of any of the foregoing methods, wherein predicting precursor to coating spallation can further include comparing a number of pixels, which correspond to calculated thermal diffusivities exceeding a predetermined threshold, with a predetermined count.

Some embodiments relate to a system for predicting precursor to coating spallation. The system includes a heat source, a thermographic camera, one or more processors, and one or more storage devices encoded with instructions that, when executed by the one or more processors, cause the system to provide heat to a first surface of a member having a coating on the first surface and/or a second surface. The instructions, when executed by the one or more processors, further cause the system to capture a time sequence of thermal images of the first surface or of the second surface of the member, each of the time sequence of thermal images comprising a two-dimensional array of pixel data, each of the two-dimensional array of pixel data corresponding to an xy-coordinate pair. The instructions, when executed by the one or more processors, further cause the system to calculate, based on the captured time sequence of thermal images, a two-dimensional array of thermal diffusivities, each of the two-dimensional array of thermal diffusivities corresponding to the xy-coordinate pair. The instructions, when executed by the one or more processors, further cause the system to compare each of the calculated thermal diffusivities of the two dimensional array of thermal diffusivities with a predetermined threshold. The instructions, when executed by the one or more processors, further cause the system to predict, based on the calculated thermal diffusivities, precursor to coating spallation at the corresponding xy-coordinate pair.

The system of the preceding paragraph can optionally include, additionally and/or alternatively, any one or more of the following features, configurations and/or additional components:

A further embodiment of the foregoing system, wherein the coating can be a thermal barrier coating.

A further embodiment of any of the foregoing systems, wherein one or more storage devices encoded with instructions that, when executed by the one or more processors, can cause the system to capture the time sequence of thermal images of the first surface of the member, thereby acting as a pulse-echo thermal-imager, and to generate the provided heat as a temporal pulse of heat.

A further embodiment of any of the foregoing systems, wherein one or more storage devices encoded with instructions that, when executed by the one or more processors, can cause the system to capture the time sequence of thermal images of the second surface of the member, thereby acting as a through-transmission thermal-imager, and to generate the provided heat as a temporal step of heat.

A further embodiment of any of the foregoing systems, wherein one or more storage devices encoded with instructions that, when executed by the one or more processors, can cause the system to output, if precursor to coating spallation is predicted, an alarm signal.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A through-transmission thermal imaging system for predicting precursor to coating spallation, the system comprising:
    a heat source configured to provide a temporal step of heat to a first surface of a member having a coating formed on the first surface and/or a second surface;
    a thermographic camera having a focal plane array comprising a two-dimensional array of pixels, each having an xy-coordinate pair corresponding to an xy-location of the member, the thermographic camera configured to receive heat conducted through the member, from the first surface to the second surface, and then radiated from the second surface of the member into the external atmosphere, and to focus the received heat onto the focal plane array, thereby forming an image of the second surface of the member, the thermographic camera further configured to capture a time sequence of thermal images of the second surface of the member, wherein the time sequence of thermal images is indicative of thermal diffusivities of the member at respective xy-locations; and
    a spallation predictor configured to predict, based on a comparison of the thermal diffusivities of the member at the respective xy-locations and a predetermined threshold, precursor to coating spallation.

2. The system of claim 1, further comprising:
    a thermal diffusivity calculator configured to calculate, based on the captured time sequence of thermal images, a two-dimensional array of thermal diffusivities, each of the two-dimensional array of thermal diffusivities corresponding to the xy-coordinate pair of one of the pixels of the two-dimensional array of pixels.

3. The system of claim 1, wherein the coating is a thermal barrier coating.

4. The system of claim 1, wherein the spallation predictor is further configured to output an alarm signal, if precursor to coating spallation is predicted.

5. The system of claim 1, wherein the spallation predictor predicts precursor to coating spallation in response to one of the calculated thermal diffusivities exceeding a predetermined value.

6. The system of claim 1, wherein the spallation predictor predicts precursor to coating spallation in response to a number of pixels, which correspond to calculated thermal diffusivities exceeding a predetermined threshold, exceeding a predetermined count.

7. The system of claim 1, wherein the heat source and the thermographic camera are configured to mount to an aircraft proximate the member having the coating.

8. The system of claim 1, wherein the coating is on the first surface of the member.

9. The system of claim 1, wherein the heat is provided in a substantially spatially uniform manner to the first surface of the member.

10. A through-transmission thermal imaging method for predicting precursor to coating spallation, the method comprising:
providing a temporal step of heat to a first surface of a member having a coating on the first surface and/or a second surface;
conducting heat through the member, from the first surface to the second surface;
radiating heat from the second surface into the external atmosphere;
capturing a time sequence of thermal images of the heat radiated into the external atmosphere from the second surface of the member, each of the time sequence of thermal images comprising a two-dimensional array of pixel data, each of the two-dimensional array of pixel data corresponding to an xy-coordinate pair;
calculating, based on the captured time sequence of thermal images, a two-dimensional array of thermal diffusivities, each of the two-dimensional array of thermal diffusivities corresponding to the xy-coordinate pair;
comparing each of the calculated thermal diffusivities of the two dimensional array of thermal diffusivities with a predetermined threshold; and
predicting, based on the calculated thermal diffusivities, precursor to coating spallation at the corresponding xy-coordinate pair.

11. The method of claim 10, further comprising:
outputting an alarm signal if precursor to coating spallation is predicted.

12. The method of claim 10, wherein predicting precursor to coating spallation comprises:
comparing the calculated thermal diffusivities with a predetermined value.

13. The method of claim 10, wherein predicting precursor to coating spallation comprises:
comparing a number of pixels, which correspond to calculated thermal diffusivities exceeding a predetermined threshold, with a predetermined count.

14. A through-transmission thermal imaging system for predicting precursor to coating spallation, the system comprising:
a heat source;
a thermographic camera;
one or more processors; and
one or more storage devices encoded with instructions that, when executed by the one or more processors, cause the system to:
provide a temporal step of heat to a first surface of a member having a coating on the first surface and/or a second surface;
conduct heat through the member, from the first surface to the second surface;
radiate heat from the second surface into the external atmosphere;
capture a time sequence of thermal images of the second surface of the member, each of the time sequence of thermal images of the heat radiated into the external atmosphere from the second surface, each of the time sequence of thermal images comprising a two-dimensional array of pixel data, each of the two-dimensional array of pixel data corresponding to an xy-coordinate pair;
calculate, based on the captured time sequence of thermal images, a two-dimensional array of thermal diffusivities, each of the two-dimensional array of thermal diffusivities corresponding to the xy-coordinate pair;
compare each of the calculated thermal diffusivities of the two dimensional array of thermal diffusivities with a predetermined threshold; and
predict, based on the calculated thermal diffusivities, precursor to coating spallation at the corresponding xy-coordinate pair.

15. The system of claim 14, wherein the coating is a thermal barrier coating.

16. The system of claim 14, wherein one or more storage devices encoded with instructions that, when executed by the one or more processors, cause the system to:
output, if precursor to coating spallation is predicted, an alarm signal.

* * * * *